United States Patent [19]
Dreier et al.

[11] Patent Number: 5,171,236
[45] Date of Patent: Dec. 15, 1992

[54] DISPOSABLE ABSORBENT ARTICLE HAVING CORE SPACERS

[75] Inventors: Kimberly A. Dreier, Cincinnati; M. Elaine Freeland, Loveland, both of Ohio

[73] Assignee: The Procter & Gamble Company, Cincinnati, Ohio

[21] Appl. No.: 811,206

[22] Filed: Dec. 20, 1991

[51] Int. Cl.⁵ .............................................. A61F 13/16
[52] U.S. Cl. .................................. 604/369; 604/385.1
[58] Field of Search ...................... 6034/358, 369, 378, 6034/379, 380, 385.1, 385.2

[56] References Cited

U.S. PATENT DOCUMENTS

| Re. 28,483 | 7/1975 | Ralph | 128/289 |
|---|---|---|---|
| 2,043,325 | 6/1936 | Jackson, Jr. | 128/284 |
| 4,382,443 | 5/1983 | Shafer et al. | 604/396 |
| 4,560,380 | 12/1985 | Tharel | 604/385 R |
| 4,662,877 | 5/1987 | Williams | 604/385 A |
| 4,731,065 | 3/1988 | Yamada | 604/355 |
| 4,891,847 | 1/1990 | Baker et al. | 4/239 |
| 4,892,536 | 1/1990 | DesMarais et al. | 604/385.2 |
| 4,895,568 | 1/1990 | Enloe | 604/385.2 |
| 4,990,147 | 2/1991 | Freeland | 604/385.2 |
| 5,037,416 | 8/1991 | Allen et al. | 604/385.1 |
| 5,062,840 | 11/1991 | Holt et al. | 604/385.1 |

FOREIGN PATENT DOCUMENTS

| 0340320A1 | 11/1089 | European Pat. Off. . |
|---|---|---|
| 0355740 | 2/1990 | European Pat. Off. . |
| 0433951A2 | 6/1991 | European Pat. Off. . |
| 2561078 | 9/1985 | France . |
| 2628761 | 9/1989 | France . |
| 9014063 | 11/1990 | PCT Int'l Appl. .................. 604/358 |
| 2074875A | 11/1981 | United Kingdom . |

Primary Examiner—David J. Isabella
Assistant Examiner—Mary Beth O. Jones
Attorney, Agent, or Firm—Larry L. Huston; Fredrick H. Braun

[57] ABSTRACT

A disposable absorbent article, such as a diaper. The disposable absorbent article has a topsheet foreshortened relative to the backsheet. This foreshortening creates a void space between the topsheet and the backsheet. Fecal material is communicated through an aperture in the topsheet to the void space.

At least two longitudinally oriented spacers are disposed in the void space to keep the void space open under the weight of the wearer's body. While the void space is open, fecal material communicated through the aperture can be transported towards the rear waistband without interuption significant obstruction, preferably isolating the fecal material from the skin of the wearer. This isolaticn provides for easier cleaning of the wearer when the disposable absorbent article is soiled and removed.

10 Claims, 2 Drawing Sheets

DISPOSABLE ABSORBENT ARTICLE HAVING CORE SPACERS

FIELD OF THE INVENTION

The present invention relates to disposable absorbent articles, particularly to disposable absorbent articles such as diapers which collect and retain fecal material, and more particularly to disposable absorbent articles having selectively disposed spacers which allow for containment and isolation of fecal material.

BACKGROUND OF THE INVENTION

Disposable absorbent articles, such as baby diapers and adult incontinence products are well known in the art. These articles represent consumer products which address the consumers' demand for products which increases the convenience of everyday living. In particular, it has long been desired to provide disposable absorbent articles which are easily removed from the wearer when soiled and minimize cleaning of the wearer after removal. A particularly desired feature of such a disposable absorbent article is to minimize cleaning of fecal material which is present on the wearer's skin after the soiled disposable absorbent article is removed.

One particular attempt to improve cleaning of fecal material from the skin of the wearer is to provide a void space in the disposable absorbent article to receive the fecal material and isolate it from the skin of the wearer. Typically, the void space is intermediate the topsheet which contacts the skin of the wearer and the core which absorbs fluid excretions, such as urine. In this arrangement, the topsheet has an aperture or other passageway which communicates the fecal material to the void space.

For example, U.S. Pat. No. 4,662,877 issued May 5, 1987 to Williams discloses a diaper having a urine impervious facing sheet with an aperture which allows waste materials to pass through the facing sheet into the absorbent portion of the diaper. The void space in the Williams diaper is formed by a convex upwardly shaped core.

Another manner in which a void space may be formed is by removing material from the core to provide a cavity. For example, U.S. Pat. No. 2,043,325 issued Jun. 9, 1936 to Jackson, Jr. discloses a sanitary pad having a pocket to receive eliminated stools. The pocket is formed by the removal of loosely packed material from the top layer of the absorbent in the pad. This construction is also shown in the catamenial napkin art, as illustrated in U.S. Pat. No. 4,731,065 issued Mar. 15, 1988 to Yamada. Yamada teaches a sanitary napkin having a recess which circumscribes the excretory organs and formed by a void space in a flexible absorbent element.

Another manner in which a void space may be formed is by layering a core made of constant thickness. For example, U.S. Pat. No. 4,560,380 issued Dec. 24, 1985 to Tharel teaches a diaper having a longitudinally oriented and centered opening formed by symmetrically opposed S-folds. The S-folds define three superimposed layers laterally extending from the longitudinally centered opening to the side margins of the diaper.

French Patent 2,561,078 published Sep. 20, 1985 in the name of LeFebvre and European Patent Application 0,355,740 published Feb. 28, 1990 in the name of Enloe teach diapers having U-shaped members defining the void space. Particularly, LeFebvre teaches a diaper having an air chamber to create the void space and which conforms to the buttocks. Enloe teaches a diaper having transversely aligned ridges or a U-shaped member made of resilient foam to inhibit the movement of fecal material. Enloe further teaches the resilient foam ridge member may be straight and cross directionally oriented.

One attempt to improve upon disposable absorbent articles having a void space is illustrated in commonly assigned U.S. Pat. No. 4,892,536 issued Jan. 9, 1990 to DesMarais et al. DesMarais et al. teaches a disposable absorbent article having a liner and a passageway therethrough. The liner is longitudinally contracted by elastic strands disposed longitudinally nonadjacent the passageway. This arrangement improves the fit of the article, particularly the liner, to the wearer.

Another attempt to improve upon disposable absorbent articles having a void space is illustrated in commonly assigned U.S. Pat. No. 4,990,147 issued Feb. 5, 1991 to Freeland. Freeland discloses a disposable absorbent article having a liner with a passageway therethrough. The liner is entirely or partially composed of elastic panels. The elastic panels register the passageway with the anal opening, minimizing the size of the passageway necessary to communicate fecal material into the void space, so that unnecessary exposure of the skin to collected fecal material is avoided.

One attempt to improve upon the teachings of Freeland is illustrated in commonly assigned U.S. Pat. No. 5,037,416 issued Aug. 6, 1991 to Allen et al. Allen et al. discloses a disposable absorbent article having an elastically extensible topsheet made of a material which can be elongated to conform to the shape of the wearer while maintaining very low contact pressure at high elongations. This arrangement provides a topsheet which closely conforms to the wearer without causing undue discomfort or irritation.

One drawback of the prior art teachings according to Williams, Tharel, DesMarais et al., Freeland, and Allen et al. is the void space does not remain open during use. While the more advanced of these teachings utilize elastic components to ensure the void space is created and registered with the anal opening, the void space may collapse when the wearer is sitting.

The prior art teachings according to Jackson, Jr., Yamada, LeFebvre, and Enloe teach support members which may hold the void space open. However, these support members teach containment of the fecal material near the passageway. Once these disposable absorbent articles are heavily loaded, subsequent loadings of fecal material may not be communicated through the opening but instead remain in contact with the skin of the wearer. This arrangement does not provide easier cleaning of the wearer since the fecal material is not isolated in the void space.

It is an object of this invention to provide a disposable absorbent article which provides for easier cleaning of fecal material from the skin of the wearer. Particularly, it is an object of this invention to provide a disposable absorbent article which not only communicates fecal material away from the wearer, but preferably isolates the fecal material in a void space.

SUMMARY OF THE INVENTION

The present invention comprises a disposable absorbent article having a front waist margin, a rear waist margin and a longitudinal centerline. The disposable absorbent article has a liquid pervious topsheet and a liquid impervious backsheet at least partially peripherally joined to one another to form a void space therebetween for receiving fecal material. An absorbent core is disposed intermediate the topsheet and backsheet.

The topsheet has an aperture for communicating fecal material into the void space. The disposable absorbent article further comprises a means for maintaining the void space when the diaper is loaded by the weight of the wearer, so that transport of fecal material away from the aperture and towards the rear waist margin is not interrupted.

The core of the disposable absorbent article may comprise an upper layer joined to the topsheet and a lower layer joined to the backsheet. The means for maintaining the void space provides a Z-direction clearance between the upper layer and the lower layer.

The means for maintaining the void space may comprise at least one, preferably at least two, longitudinally oriented spacers. One of the two longitudinally oriented spacers may be disposed on each side of the longitudinal centerline and oriented so that the spacers diverge towards the rear waist margin. A central spacer intermediate the two outboard spacers parallel and coincident with the longitudinal axis may be further provided.

BRIEF DESCRIPTION OF THE DRAWINGS

While the Specification concludes with the claims particularly pointing out and distinctly claiming the present invention, it is believed the present invention will be better understood from the following description taken in conjunction with the accompanying drawings in which:

DETAILED DESCRIPTION OF THE INVENTION

Figure 1:
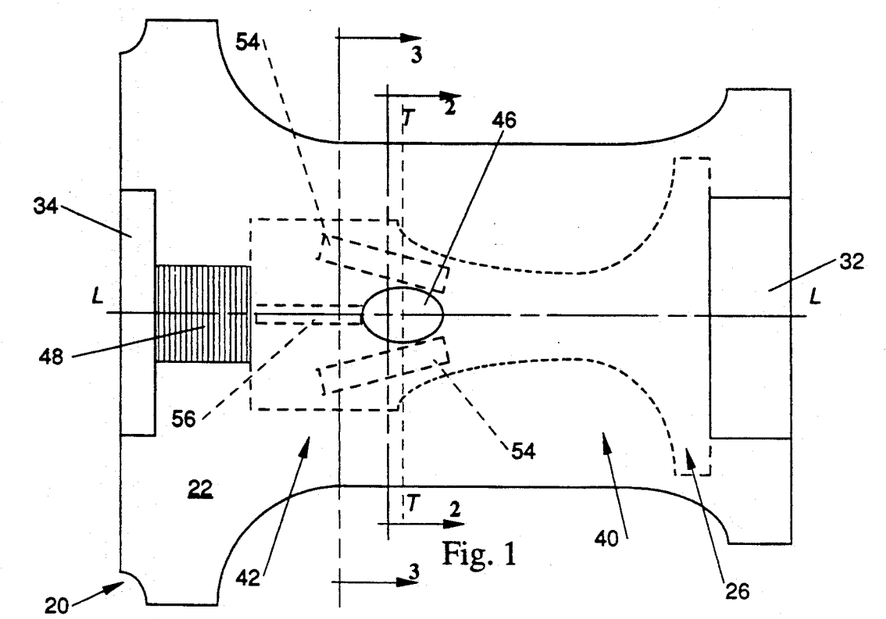
FIG. 1 is a top plan view of a diaper according to the present invention.

Referring to FIG. 1, a "disposable absorbent article" refers to a garment worn about the body of a wearer which collects body exudates. The disposable absorbent article 20 is intended to be discarded after a single use, and not laundered or otherwise restored (although certain components may be recycled or composted).

A preferred disposable absorbent article 20 according to the present invention comprises a diaper to be worn by an infant. The disposable absorbent article 20 comprises a liquid pervious topsheet 22, a liquid impervious backsheet 24, and an absorbent core 26 intermediate the topsheet 22 and the backsheet 24. The topsheet 22 and the backsheet 24 are at least partially peripherally joined to ensure the core 26 is held in the desired position. The core 26 may comprise two layers, an upper layer 26U juxtaposed with the topsheet 22 and a lower layer 26L juxtaposed with the backsheet 24. A disposable absorbent article 20 according to the present invention further comprises spacers 54 and 56 disposed between the underside of the topsheet 22 and the lower layer 26L of the core 26.

A disposable absorbent article 20 according to the present invention may further comprise elastic leg cuffs and/or barrier leg cuffs to prevent leakage of body exudates through the leg openings of the disposable absorbent article 20 while it is worn. A disposable absorbent article 20 according to the present invention preferably further comprises an elastic waist band to provide for improved fit about the waist of the wearer. A disposable absorbent article 20 according to the present invention may further comprise adhesive tape fasteners to conveniently secure the disposable absorbent article 20 about the waist of the wearer. For clarity, the elastic leg cuffs, barrier leg cuffs, elastic waist band and adhesive tape fasteners are omitted from the Figures.

However, if it is desired to incorporate such components into the disposable absorbent article 20, reference is made to commonly assigned U.S. Pat. No. 4,081,301 issued Mar. 28, 1978 to Buell which discloses a method and apparatus for applying elastic strands to a disposable absorbent article 20 to make leg cuffs; commonly assigned U.S. Pat. No. 4,909,803 issued Mar. 20, 1990 to Aziz et al. which shows how to incorporate barrier leg cuffs into a disposable absorbent article 20; commonly assigned U.S. Pat. No. 3,848,594 issued Nov. 19, 1974 to Buell which discloses how to make and incorporate adhesive tape fasteners into a disposable absorbent article 20; and commonly assigned U.S. Pat. No. 4,816,025 issued Mar. 28, 1989 to Foreman which discloses how to make a suitable waist band for a disposable absorbent article 20. The disclosures of these four patents are incorporated herein by reference for the purpose of showing how to advantageously incorporate these optional features into a disposable absorbent article 20 according to the present invention.

FIG. 1 illustrates a disposable absorbent article 20 according to the present invention laid out in a flat state having no elastic induced contraction. The topsheet 22 and the backsheet 24 generally define the periphery of the disposable absorbent article 20. The periphery is the outer perimeter and greatest extent of the disposable absorbent article 20. The periphery comprises a front waist margin 32, a rear waist margin 34, and two longitudinal side margins.

The front waist margin 32 and rear waist margin 34 are those portions of the disposable absorbent article 20 which, when worn, encircle the waist of the wearer and are generally at the highest elevation of the disposable absorbent article 20 when the wearer is in the standing position. The longitudinal side margins are those portions of the disposable absorbent article 20 periphery which connect the front and rear waist margins 32 and 34. The crotch of the disposable absorbent article 20 is that portion of the disposable absorbent article 20 which is disposed between the front waist margin 32 and rear waist margin 34 and which, when worn, is typically between the legs of the wearer.

The core 26 of the disposable absorbent article 20 does not extend into the front waist margin 32 or rear waist margin 34, so that the topsheet 22 and backsheet 24 may be joined and sealed to each other in this area or may be joined and sealed to each other in other areas. Preferably, the front and rear waist margins 32 and 34 longitudinally extend about five percent of the longitudinal dimension of the disposable absorbent article 20 from the edge of the disposable absorbent article 20 towards the transverse centerline of the disposable absorbent article 20.

As used herein, the "longitudinal" dimension, direction or axis of the disposable absorbent article 20 is that dimension, direction or axis which is aligned front to back with respect to the wearer as the disposable absorbent article 20 is worn. The "transverse" dimension, direction or axis of the disposable absorbent article 20 is generally orthogonal the longitudinal direction and sideways aligned as the disposable absorbent article 20 is worn. The transverse axis TT divides the disposable absorbent article 20 into front and rear portions 40 and 42, corresponding in position to the respective front and rear waist margins 32 and 34. The "Z-direction" is generally orthogonal both the longitudinal and transverse directions, and does not lie within the plane of the disposable absorbent article 20.

The embodiment described herein is suitable for a wearer weighing about 7.3 kilograms to about 12.2 kilograms (16 to 27 pounds) and having ischia bones spaced about 3.0 centimeters to about 7.6 centimeters (1.2 to 3.0 inches) apart. It will be understood that if the disposable absorbent article is intended for use with smaller or larger sized wearers, including adults, the disposable absorbent article will have to be scaled accordingly.

A disposable absorbent article 20 sized to fit the aforementioned range of wearers may be made having a topsheet 22 with a longitudinal dimension of about 43.8 centimeters (17.25 inches) and a backsheet 24 having a longitudinal dimension of about 46.4 centimeters (18.25 inches). The difference in longitudinal dimension between the topsheet 22 and the backsheet 24 foreshortens the topsheet 22 relative to the backsheet 24 creating a void space 52 therebetween, even when a core 26 is interposed between the topsheet 22 and the backsheet 24. The topsheet 22 and backsheet 24 according to the present invention have a transverse dimension at the crotch of about 15.9 centimeters (6.25 inches) and about 21.3 centimeters (8.4 inches) respectively.

The elements of the disposable absorbent article 20 may be assembled in any variety of configurations well known to one skilled in the art. Preferred configurations are described in commonly assigned U.S. Pat. No. 3,860,003 issued Jan. 14, 1975 to Buell, and the aforementioned commonly assigned U.S. Pat. No. 4,909,803 issued Mar. 20, 1990 to Aziz et al., which patents are incorporated herein by reference for the purpose of disclosing well known and preferred disposable absorbent article 20 configurations. In an even more preferred embodiment the configuration of the disposable absorbent article 20 conforms to the teachings of U.S. patent application Ser. No. 07/715,152 filed Jun. 13, 1991 in the name of Buell et al.

Examining the components of the disposable absorbent article 20 in more detail, the topsheet 22 and backsheet 24 are generally coextensive and at least partially peripherally joined together as noted above. As used herein the term "join" refers to the condition where a first member or component is affixed or connected to a second member or component, either directly, or indirectly where the first member or component is affixed or connected to an intermediate member or component which in turn is affixed or connected to the second member or component. The association between the first member or component and the second member or component is intended to remain for the life of the disposable absorbent article 20.

The topsheet 22 and backsheet 24 may be joined by any means well known in the art, such as adhesive bonding or heat sealing. A particularly preferred method of joining the topsheet 22 and backsheet 24 is using hot-melt adhesive such as manufactured by Century Adhesives, Inc. of Columbus, Ohio and marketed as Century 5227 or HL1258 adhesive sold by the H. B. Fuller Company of St. Paul, Minn. In a particularly preferred embodiment, adhesive joining is accomplished by longitudinally oriented adhesive bands.

The absorbent core 26 has longitudinal and transverse dimensions generally less than those of the topsheet 22 and the backsheet 24. The lower layer 26L of the absorbent core 26 may be made of a variety of sizes and shapes, such as rectangular or hourglass. The upper layer 26U of the core 26 generally matches the shape of the rear portion 42 of the topsheet 22.

As used herein the "core" refers to any component of the disposable absorbent article 20 used for absorbing and retaining body exudates. The upper layer 26U and the lower layer 26L of the absorbent core 26 each have opposed major faces and may, if desired, be encased by one or more layers of tissue, plastic, or may be coated with a release agent to reduce friction against the fecal material.

The tissue layer improves the tensile strength of the absorbent core 26 and reduces its tendency to split or clump when wetted. The tissue may further improve transverse wicking of fluids and more evenly distribute absorbed liquids throughout the absorbent core 26. A tissue layer having a basis weight of approximately 16 grams per square meter (10 pounds per 3,000 square feet) and an air permeability of approximately 30 cubic meters per minute per square meter (100 cubic feet per minute per square foot) and a differential pressure of 13 millimeters of water (0.5 inch of water) has been found to work well. Alternatively, the topsheet 22 may separately or also wrap around the core 26.

The absorbent core 26 may be made from a variety of commonly used materials such as comminuted wood pulp, typically referred to as air felt. If desired, the absorbent core 26 may further contain absorbent gelling materials as is commonly used in the art. In particular, the absorbent core 26 may be made in accordance with the teachings of commonly assigned U.S. Pat. No. 4,610,678 issued Sep. 9, 1986 to Weisman et al., which patent is incorporated herein by reference for the purpose of showing how to make an absorbent core 26 suitable for use with the present invention. Absorbent gelling materials made in accordance with commonly assigned U.S. Pat. No. Re. 32,649 issued Apr. 19, 1988 to Brandt et al. have been found suitable for use in a disposable absorbent article 20 according to the present invention.

If desired, in a particularly preferred embodiment the lower layer 26L of the absorbent core 26 may have discrete storage and acquisition zones. The storage zone has a higher average density and higher average basis weight than the acquisition zone, so that the acquisition zone may effectively and efficiently acquire rapidly discharged liquids and transport the same to the storage zone for long term containment. Such a lower layer 26L may be made in accordance with the teachings of commonly assigned U.S. Pat. No. 4,834,735 issued May 30, 1989 to Alemany et al., which patent is incorporated herein by reference for the purpose of showing how to make a particularly preferred lower layer 26L of the core 26. A very suitable core 26 material is a fibrous absorbent gelling material such as is sold under the tradename Fibersorb by the Atlantic Richfield Company of Los Angeles, Calif.

Figure 2:
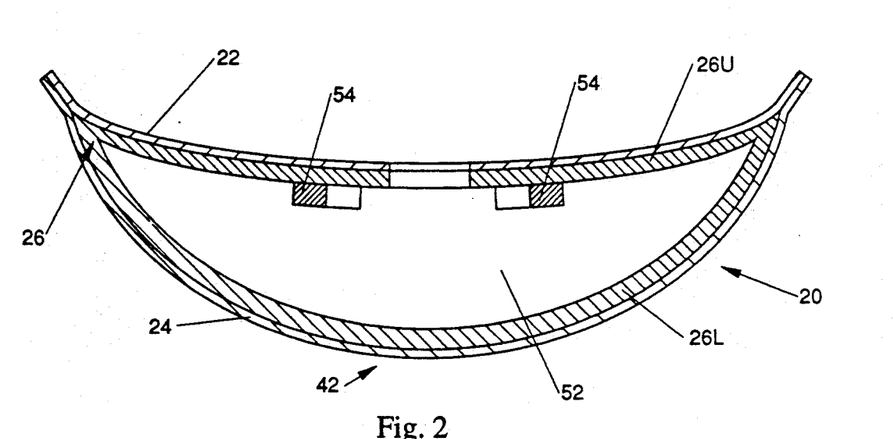
FIG. 2 is a transverse vertical sectional view taken along line 2—2 of FIG. 1.

As illustrated in FIG. 2, the core 26 comprises two separate layers, the upper layer 26U which is joined to the underside of the topsheet 22 and the lower layer 26L which is joined to the upper side of the backsheet 24. The upper and lower layers 26U and 26L of the core 26 may be adhesively joined to the topsheet 22 and backsheet 24 respectively by any attachment means well known in the art. A particularly preferred attachment means is adhesive spirals and longitudinal and transverse bands of adhesive. Particularly preferred types of adhesive are manufactured by Century Adhesives, Inc. of Columbus, Ohio as Century 5227, HL-1258 Adhesive sold by the H. B. Fuller Company of St. Paul, Minn. and XPO-9-035 adhesive manufactured by the Minnesota Mining and Manufacturing Company of St. Paul, Minn.

Preferably, the lower layer 26L of the core 26 extends the entire longitudinal dimension of the disposable absorbent article 20 between the front waist margin 32 and the rear waist margin 34, but does not intrude into either the front waist margin 32 or the rear waist margin 34. The upper layer 26U of the core 26 need only be present in the rear portion 42 of the disposable absorbent article 20.

One opposed face of the lower layer 26L of the core 26 is oriented towards the upper core 26 layer and the underside of the topsheet 22. The other opposed face of the lower layer 26L of the core 26 is oriented towards the backsheet 24, and preferably is in contacting relationship therewith. More preferably, the lower layer 26L of the absorbent core 26 is adhesively joined to the backsheet 24.

The upper layer 26U of the core 26 insulates the wearer from the impression and applied pressures of the spacers, discussed below, which occur when the wearer is sitting while wearing the disposable absorbent article 20. For this reason, the upper layer 26U of the core 26 should be present in the rear portion 42 of the disposable absorbent article 20 and particularly, but only present between the rear waist band and the aperture 46. It is not necessary that the upper layer 26U of the core 26 be present in the front portion 40 of the disposable absorbent article 20, because in a preferred embodiment the core 26 has sufficient absorptive capacity without requiring an upper layer 26U of the core 26 in the front portion 40 of the disposable absorbent article 20.

Preferably, the exposed faces of the upper layer 26U and the lower layer 26L (those faces not attached to the topsheet 22 or the backsheet 24 respectively) are well defined and do not intrude into the void space 52. Intrusion of a significant quantity of loose fibers into the void space 52 from the core 26 could interrupt (if not block) the transport of fecal material in the longitudinal direction, and prevent the isolation of such fecal material from the skin of the wearer.

Referring back to FIG. 1, the "topsheet" refers to any liquid pervious facing of the disposable absorbent article 20 which contacts the skin of the wearer while the disposable absorbent article 20 is worn and prevents substantial contact of the core 26 with the skin of the wearer. The topsheet 22 is preferably compliant, tactilely pleasant and non-irritating to the skin of the wearer. Preferably the topsheet 22 is treated to be hydrophilic, to more readily transport body exudates to the core 26.

A suitable topsheet 22 may be manufactured from materials such as porous foams, apertured plastic films, natural fibers (e.g. wood fibers or cotton fibers), synthetic fibers (e.g. polyester or polypropylene fibers) or a combination of the foregoing. A particularly preferred topsheet 22 comprises polypropylene fibers having a denier of about 2.2 and a length of about 15.9 millimeters (0.62 inches). The topsheet 22 may be manufactured according to a number of techniques and may be woven, nonwoven, spunbonded, carded, etc.

A particularly preferred topsheet 22 is carded and thermally bonded and has a weight of about 18 to about 25 grams per square meter, a minimum dry tensile strength of about 400 grams per centimeter taken in the machine direction and a minimum wet tensile strength of at least about 55 grams per square centimeter taken in the cross machine direction. A suitable topsheet 22 is marketed by Veratec, Inc., Division of International Paper Company of Walpole, Mass. under the designation P-8.

Preferably, the topsheet 22 has an elastic panel 48 intermediate the transverse centerline and the rear waist margin 34. The elastic panel 48 maintains the topsheet 22 close to the wearer, helping to maintain registration of the aperture 46 with the anal opening. The elastic panel 48 may be incorporated according to the teachings of commonly assigned U.S. Pat. No. 5,032,120 issued Jul. 16, 1991 to Freeland et al., which patent is incorporated herein by reference for the purpose of showing how to make material suitable for the elastic panel 48 and incorporate the elastic panel 48 into the topsheet 22.

If present, the elastic panel 48 is preferably transversely centered on the longitudinal centerline, and may transversely extend between the entire longitudinal side margins of the disposable absorbent article 20 or may only be about 3.8 to about 4.5 centimeters (1.5 to 1.8 inches) in width. The elastic panel may longitudinally extend from the rear waist margin 34 to the aperture 46. The elastic panel 48 is preferably about 1.3 centimeters (0.5 inches) in longitudinal dimension in an unstretched condition, and may be extended about 200 percent to a longitudinal dimension of about 5.1 centimeters (2.0 inches) when incorporated into the topsheet 22. Preferably, the elastic panel 48 longitudinally extends at least about 300 percent in the longitudinal direction. The material should extend about 200 percent under about 6 to about 8 grams of applied loading per 0.03 millimeters (0.001 inches) of thickness per unit centimeter (0.4 inches) of width. A particularly preferred elastic panel 48 may be made according to the teachings of commonly assigned U.S. Pat. No. 5,037,416 issued Aug. 6, 1991 to Allen et al., which patent is incorporated herein by reference for the purpose of illustrating a particularly preferred material of construction for the elastic panel 48.

The pervious topsheet 22 further comprises an aperture 46 centered on the longitudinal axis LL. The aperture 46 may be of any shape desired with a particularly preferred shape being an oval having a longitudinal dimension of about 5.1 centimeters (2.0 inches) and a transverse dimension of about 3.8 centimeters (1.5 inches). The rearwardmost edge of the aperture 46 is disposed at least about 15.2 centimeters (6.0 inches), and preferably about 17.8 centimeters (7.0 inches) from the rear edge of the disposable absorbent article 20 while it is worn. The aperture 46 provides a passageway for the communication of fecal material from the anal opening through the topsheet 22 into the void space 52. Preferably absorbent gelling materials are not registered with the aperture 46, so that gell-blocking does not occur when large volume urine loading occurs. Gell-blocking may cause the lower layer 26L to block the void space 52 and interrupt the transport of fecal material towards the rear waist margin 34.

The backsheet 24 is impervious to fluids, such as urine, and prevents fluids absorbed by and contained in the absorbent core 26 from wetting undergarments, clothing and bedding. As used herein the "backsheet" refers to any barrier disposed outwardly of the core 26 as the disposable absorbent article 20 is worn and which contains absorbed liquids within the disposable absorbent article 20. Preferably the backsheet 24 is flexible, compliant and readily conforms to the general shape and contour of the wearer's body.

The backsheet 24 may be a polyolefinic film, such as polyethylene, having a thickness of about 0.01 millimeters to about 0.051 millimeters (0.0005 to 0.002 inches). If desired, the backsheet 24 may be embossed or matte finished to provide a cloth-like appearance or provided with passages to permit vapor escape. A suitable backsheet 24 can be made from a blend of about 45 to 90 percent linear low density polyethylene and about 10 to 55 percent polypropylene. Exemplary backsheet films are sold by Tredegar Industries, Inc. of Terre Haute, Ind. under the designation RR8220 blend for blown films and RR5475 blend for cast films.

The spacers 54 and 56 according to the present invention are generally linear elements, having a longitudinal dimension substantially greater than the other two dimensions, and are generally longitudinally oriented. As used herein, a component is considered to be "longitudinally" oriented if it is oriented within about ±45° of the longitudinal axis LL. As used herein, a "spacer" is any component of the disposable disposable absorbent article 20 which tends to keep the void space 52 open while the weight of the wearer's body is imposed on the topsheet 22.

At least two outboard spacers 54 may be used, in conjunction with any other desired spacers 54 or 56 to provide a minimum free space of at least about 0.64 centimeters (0.25 inches) between the lower layer 26L and the upper layer 26U of the core 26, taking into account any sagging or festooning of the upper layer 26U and any intrusion of loose fibers from the core 26 into this space. It is important this minimum space between the upper and lower layers 26U and 26L is maintained under the loading of the wearer's weight while the wearer is sitting. The spacers 54 and 56 may be wrapped with a nonwoven fabric to reduce breakage or cracking of the spacers 54 and 56 and improve adhesive joining to other components.

The spacers 54 and 56 may be made of any material rigid enough to support the weight of the wearer and retain the aforementioned minimum clearance between the upper layer 26U and the lower layer 26L, but yet not provide enough resistance to compression to allow red marking of the skin to occur. Generally, as the wearer becomes heavier, spacers 54 and 56 having a greater transverse dimension are preferred, so that more resistance to compression is provided. Spacers having approximately 10 percent compression under a compressive pressure of about 1,400 kilograms per square meter (2 pounds per square inch) and which exhibit at least a 90 percent recovery have been found to work well.

The spacers 54 and 56 may be made of any foam type material, with open cell foams being preferred over closed cell foams. This preference is because open cell foams generally minimize occurrences of red marking.

Suitable materials for the spacers 54 and 56 include high internal phase emulsion foam absorbent materials. High internal phase emulsion foam absorbent materials may be made in accordance with the teachings of commonly assigned patent application Ser. No. 07/743,947, Issue Batch No. U40, filed Aug. 12, 1991 in the names of DesMarais et al., which patent application is incorporated herein by reference for the purpose of illustrating one suitable material for constructing spacers 54 and 56 according to the present invention.

High internal phase emulsion foam absorbent material spacers provide the advantages of high compressive resistance and breathability to prevent red marking. Furthermore, high internal phase emulsion foam absorbent materials are very absorbent, adding to the total capacity of the disposable absorbent article 20 and minimizing urine leakage.

However, high internal phase emulsion foam materials have certain disadvantages when used to construct the spacers 54 and 56. For example, certain of these materials may not readily bend along the major axis, making it difficult for the disposable absorbent article 20 to conform to the shape of the buttocks of the wearer. Further, these materials may be hard to machine or otherwise provide in the desired configuration and can be difficult to adhere to other components of the disposable absorbent article 20.

Rubber spacers 54 and 56 may also be utilized. If rubber spacers 54 and 56 are selected, suitable cross linked natural foam rubber sold by the F ex Company of Bristol, R.I., under the designatio: NRF has been found suitable.

Rubber spacers 54 and 56 provide the advantage of being very flexible along the major axis of the spacer. However, rubber spacers 54 and 56 have the disadvantages of being neither breathable nor absorbent, and are usually too compressible.

If desired, cross-linked polyethylene foams may be utilized for the spacers 54 and 56. Suitable foams are sold by the Voltek Company, a division of Sekisui of Lawrence, Mass. as Type S foam. These foams provide the advantages of being inexpensive and easy to mold or otherwise machine to the desired configuration. However, these foams provide the disadvantages of not being breathable and being too incompressible.

It will be apparent to one skilled in the art that several other materials are suitable for making spacers 54 and 56 according to the present invention. For example, fast acting fluid stable aggregates as disclosed in commonly assigned U.S. patent application Ser. No. 07/705,451, Issue Batch No. T39, filed May 24, 1991 in the names of Roe et al., or twisted, chemically stiffened cellulosic fibers as disclosed in commonly assigned U.S. Pat. No. 4,898,642 issued Feb. 6, 1990 to Moore et al., are feasible, which patent application and patent are incorporated herein by reference for the purpose of disclosing alternative materials suitable for constructing spacers 54 and 56 according to the present invention. Alternatively, spacers 54 and 56 according to the present invention may be made of the aforementioned Fibersorb brand material sold by the Atlantic Richfield Company.

More particularly, a disposable absorbent article 20 according to the present invention may comprise two outboard spacers 54, one disposed on each side of the longitudinal axis LL. The outboard spacers 54 are generally linear, as noted above and longitudinally oriented. More preferably, each outboard spacer 54 is oriented at an angle of about 15° from the longitudinal axis LL so that an included angle of about 30° is formed between the outboard spacers 54.

The outboard spacers 54 provide a means for maintaining a clearance between the upper layer 26U and the lower layer 26L of the core 26 when a compressive force is applied to the disposable absorbent article 20 in the Z-direction. Particularly, the outboard spacers 54 are a means for maintaining the void space 52 when the disposable absorbent article 20 is loaded by the weight of the wearer. By maintaining this void space 52, fecal material communicated to the void space 52 through the aperture 46 may be more readily longitudinally transported without blockage, obturation or occluding of the void space 52. Preferably, the fecal material is transported towards the rear waist margin 34 where the fecal material is isolated from the skin of the wearer and does not pass from the void space 52 back through the aperture 46 to the skin of the wearer.

Preferably the longitudinally oriented outboard spacers 54 diverge towards the rear waist margin 34 of the disposable absorbent article 20. It is important that any obstruction, particularly transversely oriented components, between the outboard spacers 54 is minimized, otherwise transport of fecal material away from the aperture 46 and towards the rear waist margin 34 of the disposable absorbent article 20 may be inhibited, interrupted or otherwise diminished. Preferably, the outboard spacers 54 longitudinally extend forward to at least about the front edge of the aperture 46 and longitudinally extend rearwardly of the aperture 46 towards the rear waist margin 34 back for a distance of several centimeters.

It is important that the outboard spacers 54 have a longitudinal extent at least as great as that of the aperture 46, so that the void space 52 is fully supported and open along the aperture 46. The outboard spacers 54 should not longitudinally extend into the rear waist margin 34 or transversely extend beyond the boundaries of the core 26, otherwise leakage may occur. Thus, the size and shape of the core 26 will influence the included angle between the outboard spacers 54.

The aspect ratio of the outboard spacers 54 should not be too great. If the outboard spacers 54 are too narrow in the transverse dimension relative to the Z-direction, the outboard spacers 54 may fold or collapse under the weight of the wearer. Conversely, the outboard spacers 54 should not be too small in the Z-direction, otherwise the minimum desired clearance between the upper and lower layers 26U and 26L may not be sustained.

Thus, the desired aspect ratio is a trade off between having outboard spacers 54 wide enough to support the weight of the wearer, and being tall enough to provide the aforementioned minimum clearance between the upper layer 26U and the lower layer 26L without being so thin that folding or collapse of the spacers may occur. Generally, fecal material tends to flow along the edges of the spacers. Therefore, a void space 52 having a relatively large Z-direction clearance between the upper layer 26U and the lower layer 26L, at the expense, if necessary, of a greater transverse dimension is generally preferred.

For the embodiment described herein, high internal phase emulsion foam outboard spacers 54 having longitudinal dimensions of about 15.2 centimeters (6.0 inches), transverse dimensions of about 1.27 centimeters (0.5 inches) and Z-direction dimensions of about 0.95 centimeters (0.38 inches) have been found to work well.

Referring to FIG. 2, the outboard spacers 54 are preferably attached to the underside of the upper layer 26U of the core 26. By attaching the outboard spacers 54 to the upper layer 26U, the outboard spacers 54 are generally closer to the wearer and provide better sustained fit of the outboard spacers 54 relative to the aperture 46 and hence better registry of the aperture 46 with the anal opening.

If desired, the outboard spacers 54 may be attached to the upper surface of the lower layer 26L of the core 26, but this arrangement presents several disadvantages. For example, the backsheet 24 of a disposable absorbent article 20 according to the present invention (or according to the prior art) may move relative to the topsheet 22. If the spacers are attached to the backsheet 24, even through the lower layer 26L, registry with the aperture 46 and ultimately with the anal opening may not be assured.

The outboard spacers 54 may be attached to the upper layer 26U or lower layer 26L by any means well known in the art, preferably adhesive attachment. In a preferred embodiment, the outboard spacers 54 are adhesively attached using a band of longitudinal adhesive between the spacer and the upper layer 26U. The aforementioned XPO-9-035 adhesive made by the Minnesota Mining and Manufacturing Company has been found to work well for this purpose.

Referring back to FIG. 1, if desired, a disposable absorbent article 20 according to the present invention may further comprise a central spacer 56. The central spacer 56 is parallel and coincident the longitudinal centerline and disposed in the rear portion 42 of the disposable absorbent article 20. The central spacer 56 may have a longitudinal dimension of about 5.1 to 10.2 centimeters (2 to 4 inches), transverse and Z-direction dimensions identical to those of the outboard spacers 54 and be offset somewhat towards the rear waist margin 34 from the back edge of the aperture 46.

Figure 3:
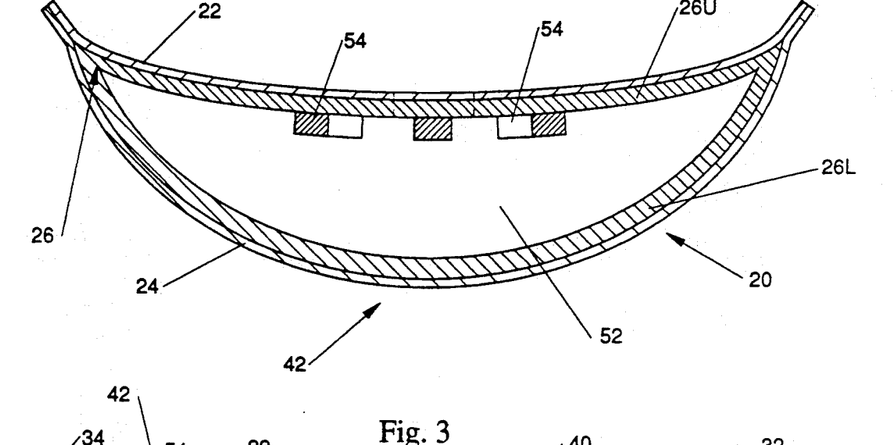
FIG. 3 is a transverse vertical sectional view taken along line 3—3 of FIG. 1.

Referring to FIG. 3, the central spacer 56 provides the advantage of reducing the amount of fecal material in the gluteal groove of the wearer, providing for easier cleaning when the soiled disposable absorbent article 20 is removed. Also, the central spacer 56 bisects the transverse span between the outboard spacers 54, preventing the upper layer 26U of the core 26 from sagging or festooning into the void space 52. The central spacer 56 should not have a greater Z-direction dimension than the outboard spacers 54, otherwise the disposable absorbent article 20 may be uncomfortable to the wearer or the central spacer 56 may fold or collapse.

Figure 4:
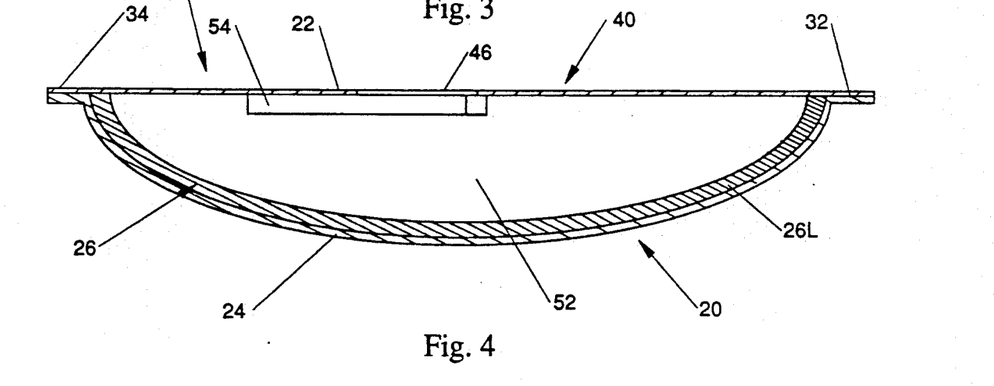
FIG. 4 is a longitudinal vertical sectional view of an alternative embodiment of a diaper according to the present invention having no upper core layer.

Several variants of the disposable absorbent article 20 according to the present invention are feasible. As illustrated in FIG. 4 for example, the upper layer 26U of the core 26 may be omitted from the rear portion 42 of the disposable absorbent article 20, as well as from the front portion 40 of the disposable absorbent article 20. This arrangement provides the advantage, particularly for the female wearer, that urine will be rapidly transmitted through the topsheet 22 but provides the disadvantage that the spacers 54 and 56 are placed more directly in contact with the buttocks of the wearer, increasing the likelihood of red marking. Furthermore, the upper layer 26U of the core 26 provides transverse stability—preventing the outboard spacers 54 from moving inwardly relative to one another and not providing support so that the anal opening is registered with the passageway.

Figure 5:
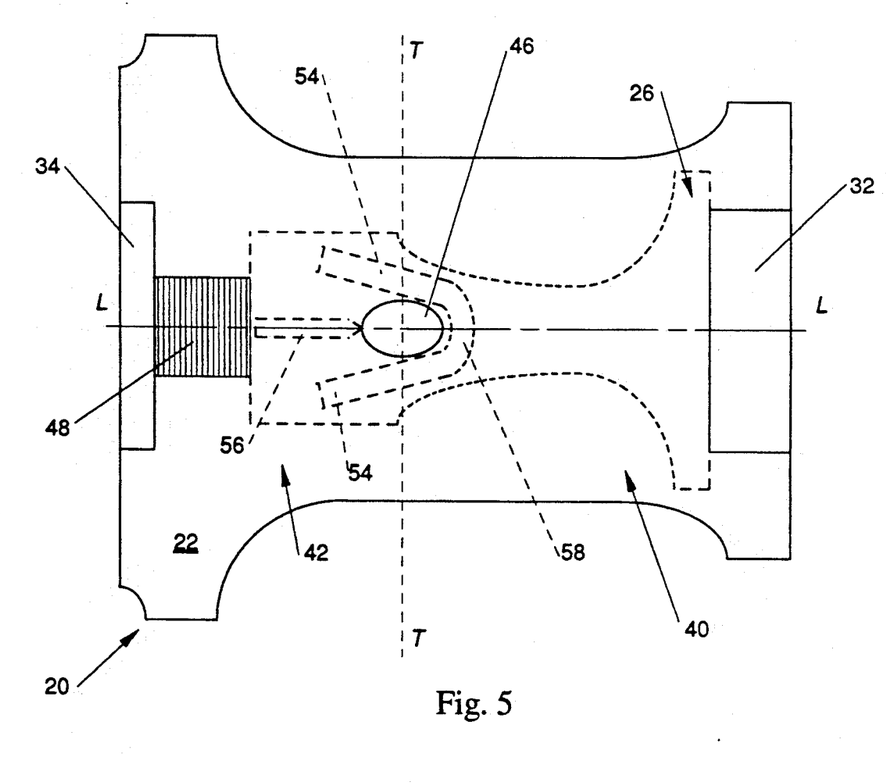
FIG. 5 is a top plan view of an alternative embodiment of the present invention having a transverse spacer between the outboard spacers and in front of the aperture.

As illustrated in FIG. 5, a disposable absorbent article 20 according to the present invention, and particularly according to the variant having no upper layer 26U of the core 26, may have a transversely oriented spacer 58 intermediate the two outboard spacers 54. The transverse spacer 58 may be joined to or separate from the outboard spacers 54.

It is, however, important the transversely oriented spacer 58 be disposed in the front portion 40 of the disposable absorbent article 20 and particularly not be disposed to the rear of the aperture 46. Any transversely oriented spacer 58 should not block the void space 52 or otherwise interrupt or prevent the transmission of fecal material from the aperture 46 towards the rear waist margin 34.

The transversely oriented spacer 58 is more important in an embodiment which does not have an upper layer 26U to provide transverse support of the outboard spacers 54, to reduce undesired transverse movement of the outboard spacers 54. While the transversely oriented spacer 58 may prevent the outboard spacers 54 longitudinally adjacent or forward of the aperture 46 from moving inwardly and pinching the scrotum of a male wearer, care must be taken the scrotum does not become lodged underneath the transverse spacer 58 and pinched.

If it is desired to incorporate a transverse spacer 58 between the outboard spacers 54, the transverse space may either be separate from or joined to the outboard spacers 54. If it is desired to join the transverse spacer 58 and outboard spacers 54, a generally U-shaped arrangement may be utilized as illustrated in FIG. 5. The embodiment of FIG. 5 has two outboard spacers 54, joined in front of the aperture 46 by a transverse spacer 58 to yield a generally U-shaped configuration. The U-shaped configuration is oriented towards the rear waist margin 34.

In another variant, the end of the central spacer 56 juxtaposed with the aperture 46 may be tapered as illustrated in FIG. 5. This taper reduces the flow resistance of the central spacer 56 to the fecal material as it is transported towards the rear waistband. This arrangement also promotes an isomeric division of the fecal material on both sides of the central spacer 56 and longitudinal axis LL, so that neither portion of the void space 52 between the central spacer 56 and either outboard spacer 54 becomes prematurely overloaded.

It will be apparent to one skilled in the art that several other variants are feasible as well. For example, the transverse division of the void space 52 by the central spacer 56 is not limited to bisecting the void space 52 as illustrated in FIGS. 1 and 3. If desired, several central spacers 56 may be interposed between the two outboard spacers 54, so long as the void space 52 remains open without significant interruption or blockage of the transmission of fecal material as noted above. In fact, a plurality of central spacers 56 fanning out from the back of the aperture 46 may be incorporated if desired.

The spacers 54, 56, and 58, and particularly longitudinally oriented spacers 54 and 56, may be modified to accommodate the curvature of the buttocks of the wearer as well For example, the outboard spacers 54 or the central spacer 56 may be transversely slit or otherwise provided with transversely oriented score lines on the tension side of the neutral axis of the spacers 54 and 56. The tension side of the spacers 54 and 56 is dictated by the curvature of the spacers around the buttocks of the wearer and is the side of the spacers 54 and 56 facing the backsheet 24. This arrangement allows the spacers 54 and 56 to curve along the longitudinal dimension to more readily and accurately conform to the buttocks of the wearer. This arrangement may also make the disposable absorbent article 20 easier to fold for packaging and shipment.

If desired, the central spacer 56 may be joined to either the upper or lower layer 26U or 26L of the core 26 and the outboard spacers 54 joined to the opposite layer 26L or 26U of the core 26. Similarly, the transverse spacer 58 may be joined to a different layer 26L or 26U than the other spacers 54 and 56.

It will be apparent that several other modifications and variants may be made by one skilled in the art. All are within the scope and intent of the appended claims.

What is claimed is:

1. A disposable absorbent article having a front waist margin, a rear waist margin, a longitudinal centerline and a Z-direction orthogonal thereto, said disposable absorbent article comprising:
   a liquid pervious topsheet;
   a liquid impervious backsheet at least partially peripherally joined to said topsheet to form a void space intermediate said topsheet and said backsheet for receiving fecal material;
   an absorbent core intermediate said topsheet and said backsheet said core comprising an upper layer joined to said topsheet and a lower layer joined to said backsheet;
   an aperture through said topsheet for communicating fecal material to the void space; and
   two longitudinally oriented spacers disposed in the rear portion of said disposable absorbent article, one said spacer being disposed on each side of said longitudinal centerline intermediate said topsheet and said core, and said longitudinally oriented spacers are joined to one of said upper layer and said lower layer in a deposition intermediate said upper layer and said lower layer.

2. A disposable absorbent article according to claim 1 wherein said two spacers diverge toward said rear waist margin.

3. A disposable absorbent article according to claim 1 wherein said spacers extend the entire longitudinal dimension of said aperture.

4. A disposable absorbent article according to claim 1 wherein said upper layer is present only in the rear portion of said disposable absorbent article and said longitudinally oriented spacers are adhered to said upper layer.

5. A disposable absorbent article having a front waist margin, a rear waist margin, a longitudinal centerline and a Z-direction orthogonal thereto, said disposable absorbent article comprising:
   a liquid pervious topsheet;
   a liquid impervious backsheet at least partially peripherally joined to said topsheet to form a void space for receiving fecal material;
   an absorbent core immediately said topsheet and said backsheet wherein said core has an upper layer juxtaposed with said topsheet and a lower layer juxtaposed with said backsheet to form a void space for receiving fecal material between said upper layer and said lower layer;
   an aperture through said topsheet for communicating fecal material to the void space; and two longitudinally oriented spacers intermediate said topsheet and said backsheet and joined to at least one of said upper layer of said core or said lower layer of said core, one said spacer disposed on each side of said longitudinal centerline.

6. A disposable absorbent article according to claim 5 further comprising a transversely oriented spacer intermediate said two longitudinally oriented spacers and disposed in the front portion of said disposable absorbent article intermediate said topsheet and said backsheet.

7. A disposable absorbent article according to claim 5 further comprising a central spacer intermediate said topsheet and said backsheet, said central spacer parallel and coincident said longitudinal axis.

8. A disposable absorbent article according to claim 5 wherein said spacers are selected from the group consisting of foam, rubber, twisted cellulosic fibers, and fluid stable aggregates.

9. A disposable absorbent article according to claim 8 wherein said spacers comprise high internal phase emulsion foam.

10. A disposable absorbent article according to claim 5 wherein said upper layer and said lower layer have a Z-direction space therebetween, said Z-direction space being on the longitudinal centerline of said disposable article, said Z-direction space being orthogonal to the longitudinal centerline of the disposable absorbent article, and having a dimension of at least about 0.64 centimeters when said spacers are under a pressure of about 1,400 kilograms per square meter.

* * * * *